United States Patent
Muliawan et al.

(10) Patent No.: US 8,884,073 B2
(45) Date of Patent: Nov. 11, 2014

(54) PROCESSES FOR PREPARING POLYTRIMETHYLENE ETHER GLYCOL

(75) Inventors: Edward Budi Muliawan, Kingston (CA); Raja Hari Poladi, Bear, DE (US); Hari Babu Sunkara, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 421 days.

(21) Appl. No.: 13/453,536

(22) Filed: Apr. 23, 2012

(65) Prior Publication Data

US 2012/0277478 A1 Nov. 1, 2012

Related U.S. Application Data

(60) Provisional application No. 61/479,185, filed on Apr. 26, 2011.

(51) Int. Cl.
| | | |
|---|---|---|
| *C07C 41/42* | (2006.01) | |
| *C07C 43/317* | (2006.01) | |
| *C07C 41/09* | (2006.01) | |
| *C07C 29/80* | (2006.01) | |
| *C07C 41/36* | (2006.01) | |

(52) U.S. Cl.
CPC ............... *C07C 41/09* (2013.01); *C07C 29/80* (2013.01); *C07C 41/36* (2013.01)
USPC .......................................... 568/619; 568/623

(58) Field of Classification Search
CPC .......... C07C 29/80; C07C 41/09; C07C 41/36
USPC ................................................. 568/619, 623
See application file for complete search history.

(56) References Cited

U.S. PATENT DOCUMENTS

| 4,232,041 | A | 11/1980 | Burk et al. |
|---|---|---|---|
| 5,847,047 | A | 12/1998 | Haynie |
| 7,582,681 | B2 | 9/2009 | Schmaus et al. |
| 7,628,999 | B2 | 12/2009 | Sunkara |
| 2002/0010374 | A1 | 1/2002 | Sunkara et al. |
| 2004/0225162 | A1 | 11/2004 | Sunkara et al. |
| 2005/0272962 | A1 | 12/2005 | Sunkara et al. |
| 2009/0169500 | A1 | 7/2009 | Sunkara |
| 2009/0175806 | A1 | 7/2009 | Modak et al. |
| 2009/0286878 | A1 | 11/2009 | Elder et al. |

FOREIGN PATENT DOCUMENTS

WO 2011011279 A2 1/2011

OTHER PUBLICATIONS

Bailey et al., Antimicrobial Properties of Some Mixed Diesters of Aliphatic Diols, Journal American Chemist's Society, vol. 53, No. 10 (1976), pp. 632-633.
Berger et al., The Antimicrobial Action of Certain Glycerol Ethers and Related Compounds, Applied Microbiology, vol. 1 (1953), pp. 146-149.
Lawan et al., Antimicrobial Efficacy of Caprylyl Glycol and Ethylhexylglycerine in Emulsion, J. Health Res., vol. 23, Issue 1 (2009), pp. 1-3.
International Patent Application, PCT Internationl Application No. PCT/US2012/034666, Mailed Nov. 30, 2012.

*Primary Examiner* — Rosalynd Keys

(57) ABSTRACT

Provided are processes for preparing low molecular weight polytrimethylene ether glycol by acid catalyzed polycondensation, neutralization, removal of unreacted monomer, and contact with filter aid. The processes can avoid hydrolysis and yet provide product substantially free of catalyst derived end groups.

9 Claims, No Drawings

PROCESSES FOR PREPARING POLYTRIMETHYLENE ETHER GLYCOL

CROSS-REFERENCE TO RELATED APPLICATIONS

This application is related to and claims the benefit of priority from U.S. Provisional Patent Application No. 61/479,185, filed Apr. 26, 2011.

FIELD OF THE INVENTION

The present invention relates to processes for preparing polytrimethylene ether glycol from 1,3-propanediol.

BACKGROUND

Polytrimethylene ether glycol and its uses have been described in the art. It can be prepared by dehydration of 1,3-propanediol or by ring opening polymerization of oxetane, typically using an acid catalyst.

For water based applications such as coatings, and personal care products, it is desirable to produce short chain or low molecular weight polytrimethylene ether glycol from the polycondensation of 1,3-propanediol. However, low molecular weight polytrimethylene ether glycol prepared by dehydration of 1,3-propanediol monomer can contain unreacted monomer in significant amounts, e.g., about 8 to 15% by weight, which is undesirable for certain applications, and removal of the monomer from the product can make the product expensive. Also, when sulfuric acid is used as a catalyst, a substantial portion of the acid is converted to the ester, alkyl hydrogen sulfate, during polycondensation and can affect the hydroxy functionality of the polymer and thereby limit its use as a reactive intermediate.

In addition, lower molecular weight polymers are more water soluble than the polymer having higher molecular weights. For this reason, it can be difficult to implement the hydrolysis step in purification of lower molecular weight polymers, because of the equilibrium reaction between the sulfate ester and glycol end groups, and therefore difficult to achieve a distinct aqueous and organic phase separation. Also, the water washing steps utilized in conventional processes can be a substantial disadvantage, because the water washing not only removes the acid present but also removes water-soluble short polyether chains. Furthermore, recovery of the soluble fraction of the polymer from aqueous solutions is desirable in order to achieve desirably high polymer yields, which can be expensive and time consuming because it requires distillation of large amounts of water and can lead to undesirably high capital, maintenance, and operating costs.

It is therefore desirable to manufacture relatively low molecular weight and water soluble polytrimethylene ether glycol free of acid catalyst and acid catalyst derived end groups (e.g. acid ester end groups) and containing less than 2.0% by weight unreacted propanediol. It is further desirable to prepare such polytrimethylene ether glycol using acid-catalyzed polymerization without the hydrolysis and/or water washing steps. The present invention is directed to these and other ends.

SUMMARY

One aspect of the invention is a process of making low molecular weight polytrimethylene ether glycol comprising:

(a) polycondensing an initial mixture comprising 1,3-propanediol and sulfuric acid at a temperature of at least about 150° C. to obtain a first reaction mixture;

(b) adding to the first reaction mixture (i) alumina, (ii) silica based filter aid, and optionally (iii) activated carbon black at temperature greater than about 120° C. and less than about 200° C. to form a second reaction mixture;

(c) distilling the second reaction mixture at a pressure of about 1 to about 40 torr at a temperature of about 120° C. to about 200° C. to obtain a third reaction mixture and a distillate containing 1,3-propanediol; and d) filtering the third reaction mixture at a temperature of about 70° C. to about 100° C. to obtain polytrimethylene glycol of number average molecular weight from about 200 to about 500 which contains less than about 0.5 weight % 1,3-propanediol, and having an acid number of less than 0.05 mg KOH/g and a turbidity of less than about 1 NTU (nephelometric turbidity unit).

Another aspect of the invention is polytrimethylene ether glycol having a number average molecular weight of from about 200 to about 300, less than about 0.5 weight % 1,3-propanediol, sulfur content less than about 10 ppm, and an APHA color value of less than about 50.

DETAILED DESCRIPTION

Disclosed herein is a process of making low molecular weight polytrimethylene ether glycol comprising the steps of:

(a) polycondensing an initial mixture comprising 1,3-propanediol and sulfuric acid at a temperature of at least about 150° C. to obtain a first reaction mixture;

(b) adding to the first reaction mixture (i) alumina, (ii) silica based filter aid, and optionally (iii) activated carbon black at temperature greater than about 120° C. and less than about 200° C. to form a second reaction mixture;

(c) distilling the second reaction mixture at a pressure of about 1 to about 40 mm Hg at a temperature of about 120° C. to about 200° C. to obtain a third reaction mixture and a distillate containing 1,3-propanediol; and (d) filtering the third reaction mixture at a temperature of about 70° C. to about 100° C. to obtain polytrimethylene glycol of number average molecular weight from about 200 to about 500 which contains less than about 0.5 weight % 1,3-propanediol, and having an acid number of less than 0.05 mg KOH/g and a turbidity of less than about 1 NTU.

In one embodiment, the distilled 1,3-propanediol from step (c) is recycled to the initial mixture of step (a) to obtain polytrimethylene glycol of number average molecular weight from about 200 to about 500 which contains less than about 0.5 weight % 1,3-propanediol and a turbidity of less than about 1 NTU.

In some embodiments the number average molecular weight can be about 200 to about 400, or about 200 to about 300.

By "low molecular weight polytrimethylene ether glycol" is meant polymer or oligomer with a number average molecular weight of from about 200 to about 500.

The 1,3-propanediol employed in the initial mixture can be obtained by any of the various chemical routes or by biochemical transformation routes. Preferred routes are described in U.S. Pat. Nos. 5,015,789, 5,276,201, 5,284,979, 5,334,778, 5,364,984, 5,364,987, 5,633,362, 5,686,276, 5,821,092, 5,962,745, 6,140,543, 6,232,511, 623,948, 6,277,289, 6,284,930, 6,297,408, 6,331,264 and 6,342,646. In some preferred embodiments, the 1,3-propanediol used as the reactant or as a component of the reactant has a purity of greater than about 99% by weight as determined by gas chromatographic analysis.

The initial mixture can comprise about 90% or more by weight of 1,3-propanediol. More typically the initial mixture can comprise 99% or more by weight of 1,3-propanediol.

The initial mixture can also contain small amounts, typically no more than about 10 weight %, and in some embodiments less than 1 weight % of other co-reactants such as 1,3-propanediol dimers. Thermal stabilizers, antioxidants and coloring materials can be added to the polymerization mixture or final product if desired.

Suitable acid polycondensation catalysts are disclosed in U.S. Published Patent Application No. 2002/0007043 A1 and in U.S. Pat. No. 6,720,459. The most preferred catalyst is sulfuric acid.

The polycondensation polymerization process can be batch, semi-continuous, continuous, etc. A suitable batch process is described in U.S Patent Application Publication No. 2002/0007043, in which the polytrimethylene-ether glycol is prepared by a process comprising the steps of: (a) providing (1) reactant, and (2) acid polycondensation catalyst; and (b) polycondensing the reactants to form a polytrimethylene ether glycol. The reaction is conducted at an elevated temperature of at least about 150° C., more typically at least about 160° C. to about 210° C., more typically about 170° C. to about 190° C.

Typically the polytrimethylene ether glycol is prepared at atmospheric pressure or below. When the polycondensation is performed at a temperature of less than about 220° C., the typical pressure is less than about 5 mm Hg (66 kPa); at a temperature of about 150° C., the typical pressure is about 100 mm Hg (13 kPa) or less.

A continuous process that can be used for preparation of the polytrimethylene ether glycols is disclosed in U.S. Pat. No. 6,720,459 in which the polytrimethylene ether glycol is prepared by a continuous process comprising: (a) continuously providing (i) reactant, and (ii) polycondensation catalyst; and (b) continuously polycondensing the reactant to form polytrimethylene ether glycol. Typically the polycondensing is carried out in two or more reaction stages. Typical temperatures, pressure ranges and steps are described in U.S. Pat. No. 6,720,459.

In one continuous process the polycondensation is carried out in an up-flow co-current column reactor and the reactant, and polytrimethylene ether glycol flow upward co-currently with the flow of gases and vapors, typically where the reactor has at least 3, at least 8, and up to 30 stages, more typically up to 15 stages. The reactant can be fed to the reactor at one or multiple locations. In another embodiment, the polycondensation is carried out in a counter current vertical reactor wherein the reactant and polytrimethylene ether glycol flow in a manner counter-current to the flow of gases and vapors. Typically this reactor has two or more stages. Typically the reactant is fed at the top of the reactor.

It is desirable to control the amount of acid polycondensation catalyst used in the processes disclosed herein, because too-high acid concentrations can lead to an undesirably high concentration of catalyst-derived end groups in the polymer and can generate high solid waste and low polymer yields. Unduly low acid concentrations are also undesirable, because they lead to polymerization reaction rates too slow to be practical. The amount of acid will typically be from about 0.1 wt. %, more typically from about 0.25 wt. % to about 1 wt. %, more typically not more than about 0.5 wt. % based on the weight of the reactants. In one embodiment in which the acid polycondensation catalyst is sulfuric acid, a suitable catalyst level has been found to be about 0.25 wt. %.

The reaction time for either batch or continuous polycondensation depends on the polymer molecular weight that is desired and the reaction temperature, with longer reaction times producing higher molecular weights. In one embodiment in which the catalyst is sulfuric acid the reaction times are typically from about 1, more typically from about 2 hours, and even more typically from about 3 hours to about 20 hours, more typically about 10 hours, and even more typically about 6 hours at 180° C.

Regardless of the conditions of the polymerization method, one aspect of the current invention is a purification procedure, which allows good quality product to be obtained without unduly time consuming, laborious and expensive hydrolysis and water washing steps. The term "good quality" in the context of this disclosure means that the product contains high dihydroxyl functionality with little or no catalyst residues or catalyst-derived polymer end groups. "High hydroxyl functionality" means that about 90% or more, preferably about 95% or more, or even 99.8% or more of the polymer molecules have two hydroxyl groups. For example, in one embodiment when sulfuric acid is used as the catalyst, it is found that the polytrimethylene ether glycol product contains from about 0 to about 10, typically about 5 milliequivalents/kg of acid ester end groups, and from about 0 to about 10 ppm sulfur, typically to about 8 ppm. The acid number of the product is less than 0.05 mg KOH/g, more typically less than 0.03 mg KOH/g.

In the processes disclosed herein, the first step in purification of the crude polytrimethylene ether glycol involves adding to the reaction mixture alumina and a silica based filter aid at or slightly below the polymerization temperatures. The addition of the alumina not only halts the polycondensation reaction but also absorbs the acid and acid ester groups present in the reaction mixture. The silica acts as a filter aid and improves the filtration rate of the product mixture containing alumina. It is found that the use of both alumina and silica results in a relatively simple process, while providing product of desirable quality for a variety of applications.

By alumina is meant aluminum oxide, $Al_2O_3$, and its hydrates or oxyhydroxides such as bayerite, gibbsite, diaspore, boehmite and pseudoboehmite. The alumina can be present in any crystalline phase such as alpha-alumina (often noted as α-alumina or α-Al2O3), gamma-alumina (often noted as γ-alumina or γ-Al2O3) as well as a myriad of alumina polymorphs. Hydrated aluminas, in particular aluminum oxyhydroxides, have the general formula γ-$AlO(OH)_x.H_2O$, wherein x is 0 to 1. When x=0 the material is specifically boehmite as compared to pseudo-boehmite; when x>0 and the materials incorporate water into their crystalline structure, they are known as pseudoboehmite. Boehmite and pseudoboehmite are also described as $Al_2O_3.zH_2O$ where, when z=1 the material is boehmite and when 1<z<2 the material is pseudoboehmite.

The amount of alumina added to the reaction mixture is typically about 2-4% by weight of the first reaction mixture.

Filter aids are inert, finely divided, microporous solids commonly used to facilitate product throughput in filtration of polymer solutions or liquid polymers by preventing plugging of the filter screen by solids suspended in the polymer. Silica based filter aids are inorganic materials that are composed primarily of silicon oxides or $SiO_2$. Suitable silica based filter aids are quartz, fumed, pyrogenic silica, colloidal silica, silica gel, diatomaceous earth or diatomite, infusorial earth, kieselguhr, perlite or other volcanic glass, and commercially available products such as Celite®, Celpure®, Harborlite and Fibra-Cel. When compared to cellulose filter aids, silica based filter aids have several advantages. Silica based filter aids are more thermally stable than cellulose and therefore can be used at much higher temperatures. In addition silica, being inorganic, absorbs less product than do other types of filter aids such as organic cellulose during filtration and increases the filtration rate.

The amount of silica based filter aid added to the reaction mixture is typically about 1 to 2% by weight of the first reaction mixture.

Both the alumina and silica can be added as a dry solid, or as an aqueous slurry. The preferred weight ratio of alumina to silica is in between 2:1 to 3:1, preferably at 2.5:1. The alumina and silica can be added either separately or simultaneously, at elevated temperature, typically with enough agitation to ensure mixing. A typical temperature range is from about 120° C. to about 200° C.

Optionally, water can be removed after the addition of the alumina but before filtration. Any conventional drying method can be used, e.g. absorption by drying agents or molecular sieves, or during the distillation step described above.

After addition of the alumina and silica, the reaction mixture is distilled under reduced pressure in the range of 1 to 40 torr and at a temperature in the range of 120 to 200° C. to remove unreacted monomer. The distillation can be carried out in a standard wiped-film evaporator, short path distillator, or in the vessel containing the second reaction mixture if it is equipped adequately with a total condenser, a condensate receiver and vacuum and heating capabilities. The distillation is continued until the product contains less than about 2%, or less than about 1%, or less than about 0.5% by weight of total product.

The low molecular weight polytrimethylene ether glycol containing very low levels of unreacted monomer is useful as a reactive intermediate or as a low volatile organic content (VOC) ingredient in water-borne coating formulations.

All or part of the distilled monomer can be recovered and recycled back as part of the feed to the initial mixture. The typical weight ratio of virgin PDO to recycled PDO in the feed is from about 9:1 to 8:1. It is found that the PDO recovered from the distillation of the second reaction mixture containing both alumina and silica, require no further treatment and when used as such result in a product having desirably low color, in some embodiments with an APHA value as low as 50, or lower. Recycling the PDO without any further treatment also reduces the cost of manufacturing significantly.

Next, the reaction mixture is filtered. The filtration can be performed by any filtration method known in the art. For example, filtration under gravity, centrifugal filtration, or pressure filtration can be used. Filter presses, candle filters, pressure leaf filters or conventional filter papers can also be used for the filtration, which can be carried out batchwise or continuously. Additional filter aid material can be used during the filtration process. The spent filter cake can be disposed as a solid waste or it can be post processed to recover product. Additionally filter aid of any type can be added at this step to enhance filtration, or precoated on filter paper. The filtration step can be repeated one or more times until the desired turbidity is achieved.

The purification process not only removes the sulfuric acid catalyst present in the polymer, but surprisingly removes the catalyst-derived polymer end groups even in the absence of a hydrolysis step. In the context of this disclosure "catalyst derived polymer end groups" refers to end groups that are formed directly from the catalyst or from decomposition products of the catalyst. For example, when the catalyst is hydroiodic acid, the end groups found in prior art processes are iodide; in the case of sulfuric acid catalyst, the end groups found in prior art process are sulfate acid esters. The products of the processes disclosed herein typically contain from about 0 to about 10, more typically from about 0 to about 5 ppm sulfur. Thus the end groups are almost exclusively hydroxyl and small amounts of olefinic unsaturation. "Almost exclusively hydroxyl" means that about 90% or more, preferably about 95% or more, or even 99.8% or more of the end groups are hydroxyl. That is, the polymers typically contain from about 0 to about 10, more typically from about 0 to about 8 milliequivalents/kg of non-hydroxylic or non-olefinic end groups.

Thus the processes disclosed herein provide a relatively high purity polytrimethylene ether glycol having a number average molecular weight typically about 200 to about 300, or about 200 to about 270.

The most outstanding benefits of the processes disclosed herein are manifest when the process is operated to obtain low molecular weight polytrimethylene ether glycol that is water soluble. This is because for polytrimethylene ether glycol in the number average molecular weight of from about 200 to about 500, known purification processes requiring hydrolysis and water washing steps can be difficult to accomplish because of the presence of water sensitive oligomers. This can not only cause the hydrolysis step to be difficult and time consuming but also can lead to yield loss.

The products produced by the processes disclosed herein typically have a color of less than about 50 APHA, and end group unsaturation less than about 15 meq/kg. The color of the products can be further improved, if desired, by the addition of a color-reducing aid such as activated carbon black. One suitable method is disclosed in U.S. Patent Application No. 2004/022516, filed Aug. 5, 2003.

In a typical embodiment where the acid polycondensation catalyst is sulfuric acid, polytrimethylene ether glycol obtained by a process disclosed herein is found to have very low levels of acid ester end groups, typically from about 0 to about 10, more typically to about 5 milliequivalents/kg of acid ester end groups, and levels of sulfur typically from about 0 to about 10 ppm, more typically to about 8 ppm or to about 5 ppm.

EXAMPLES

Example 1

In a 50 gallon glass-lined reactor equipped with a condenser and an agitator, 120 kg of bio-based PDO (1,3-propanediol monomer, DuPont and Tate & Lyle Bioproducts) was charged. The reactant was heated up to 180° C. with agitation speed of 50 rpm and sub-surface $N_2$ sparging of 5 L/min. When the reactant temperature reached 180° C., 254 g (0.2% by weight) of 98% sulfuric acid was added into the reactor. This marked the start of polymerization. Polymerization proceeded at 180° C. without any $N_2$ sparging. The reaction volatiles were condensed in the condenser and polymer product was accumulated in the reactor. Polymerization was allowed to progress for 420 minutes. At the end of polymerization, the reactor temperature was reduced to 150° C. with $N_2$ sparging on the head space of the reactor. 2.7 kg of Pseudoboehmite alumina (BASF G-250 low density alumina gel) and 1.4 kg of silica-based filter aid (Celite Hyflo Super Cel®) were added into the reactor when the temperature has reached 150° C. After the solids addition, distillation of monomer took place by applying 30-40 torr of vacuum with 1-5 L/min of sub-surface $N_2$ sparging and increasing the reactor temperature to between 170° C. and 180° C. The distillate containing mostly PDO was condensed and collected for recycle. After about 11 kg of distillate has been collected, the vacuum is released and the temperature reduced to 80° C. for the filtration step, which is conducted in a standard Neutsche type filter. During the filtration step, the pseudoboehmite alumina was removed from the polymer in the presence of the silica based filter aid by re-circulating the polymer back into the filter several times until a turbidity of less than 1 NTU was achieved (measured with a Thermo Scientific Orion AQUAfast® IV Advanced Turbidity Meter). The filtration rate with silica based filter aid was 78 kg/hour.

Comparative Example

In a 50 gallon glass-lined reactor equipped with a condenser and an agitator, 120 kg of bio-based PDO (1,3-propanediol monomer, DuPont and Tate & Lyle Bioproducts) was charged. The reactant was heated up to 180° C. with agitation speed of 50 rpm and sub-surface $N_2$ sparging of 5 L/min. When the reactant temperature reached 180° C., 254 g of 98% sulfuric acid was added into the reactor. This marked the start of polymerization. Polymerization proceeded at 180° C. without any $N_2$ sparging. The reaction volatiles were condensed in the condenser and polymer product was accumulated in the reactor. Polymerization was allowed to progress for 420 minutes. At the end of polymerization, the reactor temperature was reduced to 100° C. with $N_2$ sparging on the head space of the reactor. 2.7 kg of Pseudoboehmite alumina (BASF G-250 low density alumina gel) and 1.4 kg of cellulose based filter aid (Solka Floc® Grade 40 from International Fiber Corporation, North Tonawanda, N.Y.) were added into the reactor at 100° C. for 3 hours and the reaction mixture was filtered. The filtration step was conducted in a standard Neutsche type filter. During the filtration step, the pseudoboehmite alumina was removed from the polymer in the presence of the cellulose based filter aid by re-circulating the polymer back into the filter several times until a turbidity of less than 1 NTU was achieved. The filtration rate with this filter aid was 20 kg/hour suggesting that this filter aid was not as effective as silica based filter aid and also thermally unstable at the high temperature conditions used for Example 1 (>120° C.).

Example 2

The equipment and polymerization procedures were the same as in Example 1 except for the feed. 112 kg of virgin bio-based 1,3-propanediol monomer was charged and mixed with 8 kg of distillate that was collected from Example 1. The reactant was heated up to 180° C. with agitation speed of 50 rpm and sub-surface $N_2$ sparging of 5 L/min. When the reactant temperature reached 180° C., 254 g of 98% sulfuric acid was added into the reactor. This marked the start of polymerization. Polymerization proceeded at 180° C. without any $N_2$ sparging. The reaction volatiles were condensed in the condenser and polymer product was accumulated in the reactor. Polymerization was allowed to progress for 420 minutes. At the end of polymerization, the reactor temperature was reduced to 150° C. with $N_2$ sparging on the head space of the reactor. 2.7 kg of Pseudoboehmite alumina and 1 kg of silica-based filter aid were added into the reactor when the temperature has reached 150° C. After the solids addition, distillation of monomer took place by applying 30-40 torr of vacuum with 1-5 L/min of sub-surface $N_2$ sparging and increasing the reactor temperature to between 170° C. and 180° C. The distillate containing mostly PDO was condensed and collected. After about 14 kg of distillate has been collected, the vacuum is released and the temperature reduced to 80° C. for the filtration step. During the filtration step, the pseudoboehmite alumina was removed from the polymer in the presence of the silica based filter aid by re-circulating the polymer back into the filter several times until a turbidity of less than 1 NTU was achieved.

Example 3

9,000 kg of bio-based 1,3-propanediol monomer and 18.5 kg of 98% sulfuric acid were charged in a 3,000 gal glass lined reactor equipped with a condenser and an agitator. The reactant mixture was heated up to 180° C. with agitation speed of 60 rpm and a sub-surface $N_2$ sparging of 200 L/min. The start of heat up was taken as the start of polymerization time. During the polymerization, the reaction volatiles were condensed in the condenser and polymer product was accumulated in the reactor. Polymer samples were taken periodically and their viscosities were analyzed to track the progress of molecular weight growth during the polymerization. Once the target viscosity of 100 centipoise had been reached, the temperature was reduced to 160° C. with $N_2$ sparging on the head space of the reactor. 190 kg of Pseudoboehmite alumina and 75 kg of silica-based filter aid were added into the reactor when the temperature has reached below 165° C. After the solids addition, distillation of monomer took place by applying 10-40 torr of vacuum with 20-50 L/min of sub-surface $N_2$ sparging and increasing the reactor temperature to 186° C. The distillate containing mostly PDO was condensed and collected for recycle. Polymer samples were taken periodically and the PDO content was analyzed by using a GC. After the PDO content has reached below 0.5 wt. %, the vacuum is released and the temperature reduced to 100° C. for the filtration step, which took place in a 1,000 gal Rosenmound-type filter. During the filtration step, the pseudoboehmite alumina was removed from the polymer in the presence of the silica based filter aid by re-circulating the polymer back into the filter several times until a turbidity of less than 1 NTU was achieved.

Example 4

The equipment and procedures were the same as in Example 3 except for the feed and addition of carbon black to improve the color of final product. 8,000 kg of virgin bio-based 1,3-propanediol monomer and 1,000 kg of distillate that was collected from example 3 and 18.5 kg of 98% sulfuric acid were charged into the reactor. The reactant mixture was heated up to 180° C. with agitation speed of 60 rpm and a sub-surface $N_2$ sparging of 200 L/min. The start of heat up was taken as the start of polymerization time. During the polymerization, the reaction volatiles were condensed in the condenser and polymer product was accumulated in the reactor. Polymer samples were taken periodically and their viscosities were analyzed to track the progress of molecular weight growth during the polymerization. Once the target viscosity has been reached, the temperature was reduced to 160° C. with $N_2$ sparging on the head space of the reactor. The total sulfur level in the reaction mixture was analyzed before the solids addition and was found to be 1386 ppm. 190 kg of Pseudoboehmite alumina, 75 kg of silica-based filter aid, and 15 kg of activated carbon black were added into the reactor when the temperature has reached below 165° C. After the solids addition, distillation of monomer took place by applying 10-40 torr of vacuum with 20-50 L/min of sub-surface $N_2$ sparging and increasing the reactor temperature to 186° C. The distillate containing mostly PDO was condensed and collected for recycle. Polymer samples were taken periodically and the PDO content was analyzed by using a GC. After the PDO content has reached below 0.5 wt. %, the vacuum is released and the temperature reduced to 100° C. for the filtration step. During the filtration step, the pseudoboehmite alumina and carbon black were removed from the polymer in the presence of the silica based filter aid by re-circulating the polymer back into the filter several times until a turbidity of less than 1 NTU was achieved.

The qualities of the product obtained from these examples are tabulated in Table 1. The product color was determined using Hunter Lab Color Quest Colorimeter and expressed as APHA index. The turbidity was determined using Thermo Scientific Orion AQUAfast® IV Advanced Turbidity Meter and expressed in NTU unit. The acid number was determined by titration with a base. The amount of total sulfur (from sulfuric acid and acid esters) in the polymer was determined by analyzing the samples using a wavelength dispersive X-ray fluorescence spectroscopy (PANalytical Model PW2400 WDXRF spectrometer).

TABLE 1

Summary of product quality data

|  | Example 1 | Example 2 | Example 3 | Example 4 |
|---|---|---|---|---|
| Mn product, g/mol | 247 | 246 | 268 | 265 |
| PDO final product, wt % | 2.15 | 1.27 | 0.33 | 0.3 |
| Color final product, APHA | 31 | 54 | 14 | 9 |
| Turbidity, NTU | 0.4 | 0.4 | 0.13 | 0.11 |
| Sulfur, ppm | 1 | 1 | 8 | 3 |
| Acid number, mg KOH/g | 0.024 | 0.020 | 0.005 | 0.003 |
| Viscosity @ 25° C., cP | 107.5 | 107.8 | 112.7 | 109.2 |

What is claimed is:

1. A process of making low molecular weight polytrimethylene ether glycol comprising the steps of:
   (a) polycondensing an initial mixture comprising 1,3-propanediol and sulfuric acid at a temperature of at least about 150° C. to obtain a first reaction mixture;
   (b) adding to the first reaction mixture (i) alumina, (ii) silica based filter aid, and optionally (iii) activated carbon black at temperature greater than about 120° C. and less than about 200° C. to form a second reaction mixture;
   (c) distilling the second reaction mixture at a pressure of about 1 to about 40 torr and a temperature of about 120° C. to about 200° C. to obtain a third reaction mixture and a distillate containing 1,3-propanediol; and
   (d) filtering the third reaction mixture at a temperature of about 70° C. to about 100° C. to obtain polytrimethylene glycol of number average molecular weight from about 200 to about 500 which contains less than about 0.5 weight % 1,3-propanediol and has an acid number of less than 0.05 mg KOH/g and a turbidity of less than about 1 NTU.

2. The process of claim 1 wherein the distillate containing 1,3-propanediol from step (c) is recycled to the initial mixture of step (a).

3. The process of claim 1 wherein the third reaction mixture contains less than about 1% by weight 1,3-propanediol.

4. The process of claim 1 wherein step (d) is repeated.

5. The process of claim 1 wherein the amount of sulfuric acid in step (a) is less than about 0.3% by weight.

6. The process of claim 1 wherein the polytrimethylene ether glycol has a molecular weight of from about 200 to about 300.

7. The process of claim 1 wherein the initial mixture contains recovered 1,3-propanediol.

8. The process of claim 1 wherein step (c) is performed at about 120 to about 180° C. and the total combined amount of alumina and silica is less than about 5% by weight of the first reaction mixture.

9. The process of claim 8 wherein the weight ratio of alumina to silica is within the range from 2:1 to 3:1.

* * * * *